US006865418B2

(12) United States Patent
Merry

(10) Patent No.: US 6,865,418 B2
(45) Date of Patent: Mar. 8, 2005

(54) DOCKING STATION FOR DEFIBRILLATOR

(75) Inventor: Rodney Merry, Woodinville, WA (US)

(73) Assignee: Medtronic Physio-Control Corp., Redmond, WA (US)

( * ) Notice: Subject to any disclaimer, the term of this patent is extended or adjusted under 35 U.S.C. 154(b) by 369 days.

(21) Appl. No.: 10/091,631

(22) Filed: Mar. 4, 2002

(65) Prior Publication Data
US 2003/0167074 A1 Sep. 4, 2003

(51) Int. Cl.[7] .............................. A61N 1/39; B01L 9/02; B62B 3/00; H05K 7/00
(52) U.S. Cl. .......................... 607/5; 361/679; 361/683; 280/47.34; 312/209
(58) Field of Search .............................. 607/5; 361/679, 361/683, 686; 312/209; 280/47.34, 47.35; 128/897

(56) References Cited

U.S. PATENT DOCUMENTS

| D263,995 S | * | 4/1982 | Steele ........................ D24/185 |
| 4,583,795 A | * | 4/1986 | Brown et al. ................ 312/209 |
| 5,248,264 A | | 9/1993 | Long et al. .................. 439/347 |
| 5,335,651 A | * | 8/1994 | Foster et al. ........... 128/202.13 |
| 5,375,604 A | | 12/1994 | Kelly et al. .................. 600/301 |
| 5,488,537 A | | 1/1996 | Heald et al. ................. 361/684 |
| 5,765,842 A | * | 6/1998 | Phaneuf et al. .......... 280/47.35 |
| 5,829,997 A | | 11/1998 | Okano et al. ................ 439/310 |
| 5,876,351 A | | 3/1999 | Rohde ......................... 600/523 |
| 5,921,697 A | | 7/1999 | Karl et al. ................... 403/181 |
| 5,933,321 A | | 8/1999 | Ruch et al. .................. 361/686 |
| 5,946,186 A | | 8/1999 | Karl et al. ................... 361/686 |
| 5,957,838 A | | 9/1999 | Rantala ....................... 600/300 |
| 5,997,323 A | | 12/1999 | Youn ........................... 439/159 |
| 6,163,722 A | * | 12/2000 | Magin ............................. 607/5 |
| 6,183,417 B1 | | 2/2001 | Geheb et al. ................ 600/301 |
| 6,185,095 B1 | | 2/2001 | Helot et al. ................. 361/686 |
| 6,221,012 B1 | | 4/2001 | Maschke et al. ............ 600/301 |
| 6,227,518 B1 | | 5/2001 | Sun ............................. 248/923 |
| 6,280,212 B1 | | 8/2001 | Nguyen et al. .............. 439/157 |
| 6,310,766 B1 | | 10/2001 | Bae ............................. 361/681 |
| 6,594,146 B2 | * | 7/2003 | Frangesch et al. .......... 361/686 |
| 6,721,178 B1 | * | 4/2004 | Clark et al. ................. 361/686 |
| 2003/0076015 A1 | * | 4/2003 | Ehrenreich et al. ......... 312/209 |

* cited by examiner

Primary Examiner—Carl Layno
(74) Attorney, Agent, or Firm—Shumaker & Sieffert P.A.

(57) ABSTRACT

A docking station can engage a medical device such as a defibrillator. In a typical application, the docking station is mounted to a crash cart, and the medical device can be docked or undocked from the docking station. When the medical device is docked with the docking station, the medical device is held securely. In one embodiment, the docking station includes a base and a platform that supports the medical device, and the platform has at least some freedom to rotate relative to the base.

32 Claims, 11 Drawing Sheets

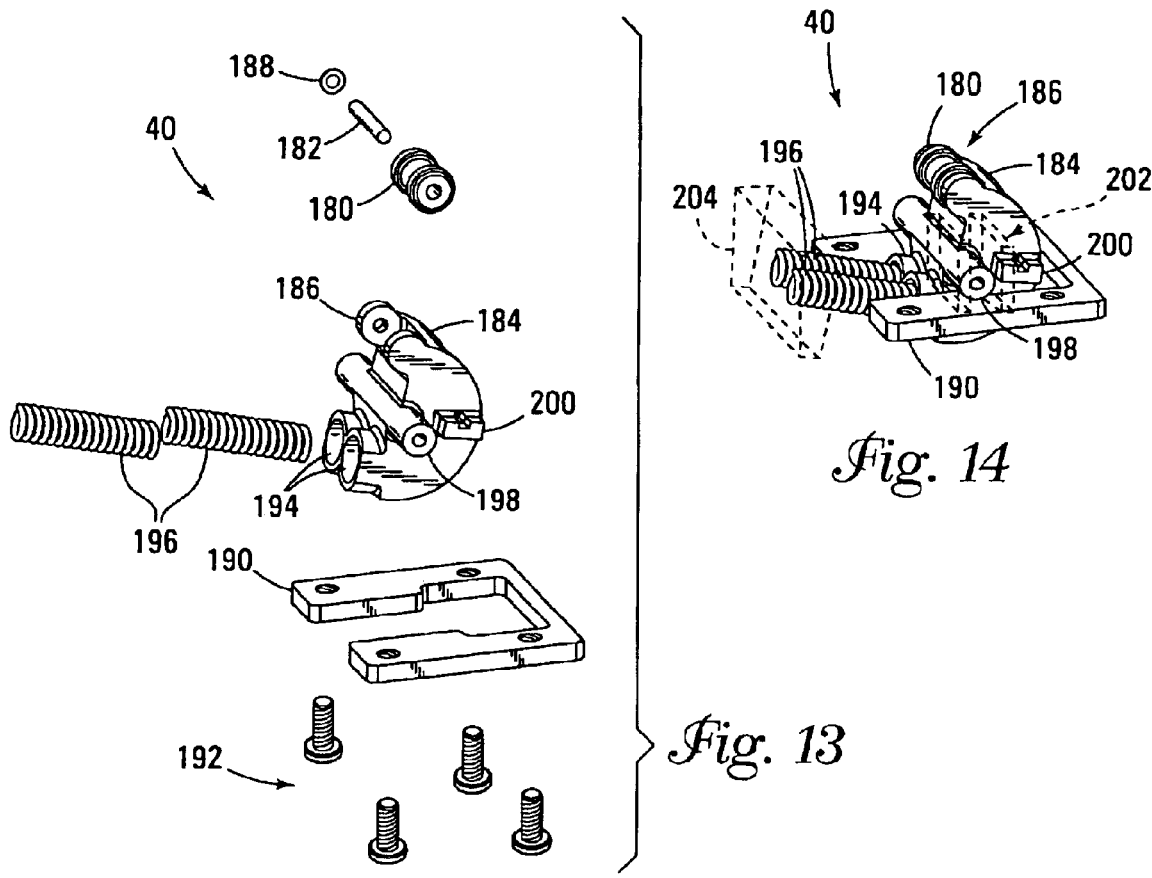
Fig. 13
Fig. 14
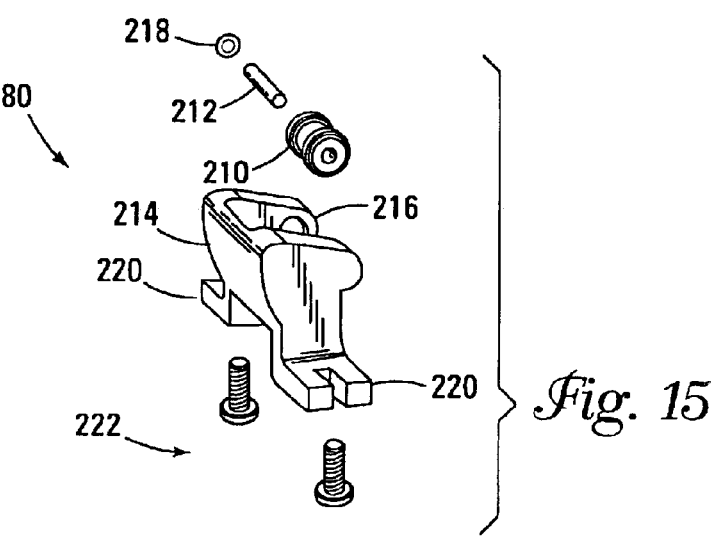
Fig. 15

DOCKING STATION FOR DEFIBRILLATOR

TECHNICAL FIELD

The invention relates to medical devices, and more particularly, to portable medical devices, such as defibrillators, that may be mounted to another structure.

BACKGROUND

Cardiac arrest and ventricular fibrillation are examples of life-threatening medical conditions that may be treated with external defibrillation. External defibrillation includes applying electrodes to the patient's chest and delivering an electric shock to the patient to depolarize the patient's heart and restore normal sinus rhythm. The chances that a patient's heart can be successfully defibrillated increase significantly if a defibrillation shock is applied quickly.

A full-featured defibrillator is standard equipment for most modern hospitals. In many cases, hospitals mount the defibrillator on a mobile cart called a "crash cart." A typical crash cart has several drawers that hold various instruments, medicines and supplies that are used by medical personnel. Some hospitals are equipped with several defibrillators mounted on crash carts. The crash carts may remain in a central location so that they may be quickly brought to the patient in need, wherever he or she may be.

Because a patient undergoing cardiac arrest or ventricular fibrillation has an urgent need, the defibrillator must be transported to the patient rapidly. A typical crash cart includes wheels so that it may be moved rapidly. In the rush to bring the defibrillator to the patient, there is a risk that the crash cart may swerve or collide with obstacles while being rushed to the patient. In such circumstances, it is important that the defibrillator not be accidentally dislodged from the crash cart.

Some hospital venues are very cramped, and a crash cart compounds the cramped conditions. When the defibrillator is mounted to the crash cart, it may be difficult to get the defibrillator close to the patient, or to orient the defibrillator so that it may be easily operated by the medical personnel.

SUMMARY

In general, the invention is directed to a docking station that can engage with a medical device such as a defibrillator. In a typical application, the docking station is mounted to a crash cart with fasteners such as bolts or screws. The medical device can easily be docked and undocked from the docking station. While docked, the medical device is held securely. Coupling mechanisms such as roller clamps engage the medical device and hold the device in place.

The medical device may also be rotated while docked. The docking station may include a base that is coupled to the crash cart and a platform that supports the medical device. The platform may have some freedom of rotation relative to the base, and the medical device may be rotated by rotating the platform.

In one embodiment, the invention is directed to a device comprising a platform, one or more coupling mechanisms and a base. In an exemplary embodiment described below, the platform is in the form of a "cover" supported by the base. The platform has some freedom to rotate relative to the base. The platform supports a medical device and the coupling mechanism engages and holds the medical device on the platform. The coupling mechanism may be, for example, a roller clamp. In an exemplary embodiment described below, three roller clamps hold the medical device, and one of the roller clamps is spring-loaded.

The device may include structure that assists the rotation of the platform relative to the base, such as a turntable. The device may also include structures that give the platform freedom to rotate in steps relative to the base.

In another embodiment, the invention is directed to a method. The method comprises engaging a medical device with a coupling mechanism on a docking station, holding the medical device with the coupling mechanism and rotating at least one portion of the docking station relative to another portion of the docking station. In an exemplary embodiment described below, the medical device may be held with a coupling mechanism such as a spring-loaded roller clamp. The roller clamp may retract when the coupling mechanism engages the medical device, and may extend to hold the medical device.

In a further embodiment, the invention is directed to a device comprising a platform, and at least two coupling mechanisms. The platform supports the medical device. The coupling mechanisms engage different sides of the medical device. The coupling mechanism may be, for example, roller clamps, and one or more of them may be spring-loaded. The device may also include a base coupled to the platform, the platform having some freedom to rotate relative to the base.

In an additional embodiment, the invention comprises a device comprising a platform and a base. Either the platform or the base is coupled to a crown, that is, a crown-like structure. The other of the platform and the base is coupled to a spring mechanism. The spring mechanism engages the crown. As a result, the rotation of the platform relative to the base is resisted by the engagement of the spring mechanism and the crown. Even though the rotational freedom of the platform relative to the base is restricted, the platform may have freedom to rotate 360 degrees relative to the base. Furthermore, the spring mechanism may deform when the platform is rotated relative to the base. In an exemplary embodiment described below, the spring mechanism and the crown cooperate to give the platform freedom to rotate in steps relative to the base.

In another embodiment, the invention is directed to an apparatus. The apparatus includes a crash cart, a base coupled to the crash cart and a platform coupled to the base. The platform supports a medical device and has some freedom to rotate relative to the crash cart.

In an added embodiment, the invention is directed to a defibrillator that includes docking structures that engage coupling mechanisms of a docking station. The docking structures may be, for example, recesses that correspond to the coupling mechanisms on the docking station.

The invention can provide one or more advantages, including security in transportation of a medical device. When docked to a docking station mounted to a crash cart, for example, the crash cart may be moved without dislodging the medical device from the crash cart. The medical device may easily be undocked from the docking station, which is advantageous in situations where the medical device needs to be taken to a place that cannot accommodate a crash cart.

While the medical device is docked to the docking station, the medical device can be rotated. It is not necessary to rotate the crash cart to orient the medical device in a desired direction. In one of the embodiments described below, the platform rotates in discrete steps relative to the base. Stepped rotational freedom prevents the medical device from swiveling uncontrollably when docked and also resists torques that may be applied when an operator operates the controls of the medical device.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 13 is an exploded view of a front clamp.

FIG. 14 is a perspective view of the assembled and mounted front clamp of FIG. 13.

FIG. 15 is an exploded view of a rear clamp.

DETAILED DESCRIPTION

Figure 1:
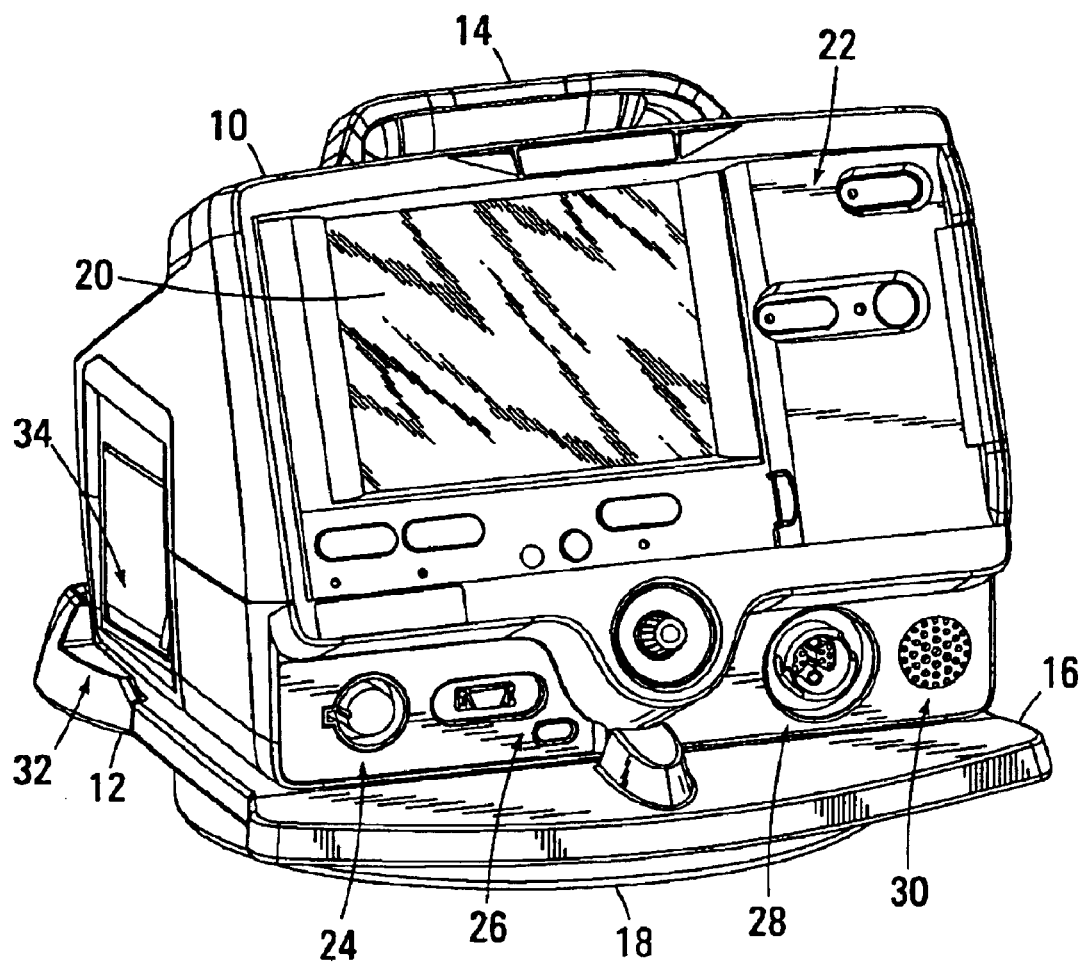
FIG. 1 is a perspective view of a defibrillator engaged with a docking station.

FIG. 1 shows a defibrillator 10 engaged with a docking station 12. Docking station 12 may be mounted to a crash cart (not shown in FIG. 1), or similar structure. As will be shown below, defibrillator 10 may be engaged with a docking station 12 very quickly, and may also be disengaged from docking station 12 quickly. When engaged with docking station 12, defibrillator 10 is held securely by docking station 12, and defibrillator 10 may be transported rapidly on the crash cart without becoming dislodged. When disengaged from docking station 12, however, defibrillator 10 is portable and may be carried by a handle 14 to any convenient site.

As will be described in more detail below, the exterior of docking station 12 principally comprises a cover 16 and a base 18. Cover 16 serves as a platform that supports defibrillator 10. Base 18 supports cover 16.

Defibrillator 10 engages coupling mechanisms (not shown in FIG. 1), such as roller clamps, that are attached to cover 16. Cover 16 can rotate relative to base 18, which is stationary relative to the crash cart. As will be described below, base 18 may be securely fastened to crash cart with fasteners such as screws, clamps, rivets or the like. By turning defibrillator 10, medical personnel rotate cover 16 relative to base 18. In this way, medical personnel can rotate defibrillator 10 to a desired orientation on the crash cart.

In addition, base 18 serves as a pedestal to elevate defibrillator 10 above the surface of the crash cart. In the exemplary application shown in FIG. 1, base 18 raises cover 16 about one inch (2.5 cm) above the surface of the crash cart. This extra space may accommodate cables and cords that may be attached to defibrillator 10, and prevent the cables and cords from binding under cover 16 when cover 16 and defibrillator 10 are turned.

Notably, cover 16 maintains a low profile. Cover 16 preferably does not obstruct display 20 or interfere with the operation of defibrillator controls 22. Nor does cover 16 interfere with front-mounted inputs or outputs, such as electrocardiogram connector 24, infrared data access 26, defibrillator electrode receptacle 28 or speaker 30. In the embodiment shown in FIG. 1, cover 16 defines a notch 32 that permits access to a built-in printer 34 of defibrillator 10. Docking station 12 therefore secures defibrillator 10 to the crash cart but does not interfere with the operation of defibrillator 10.

Figure 2:
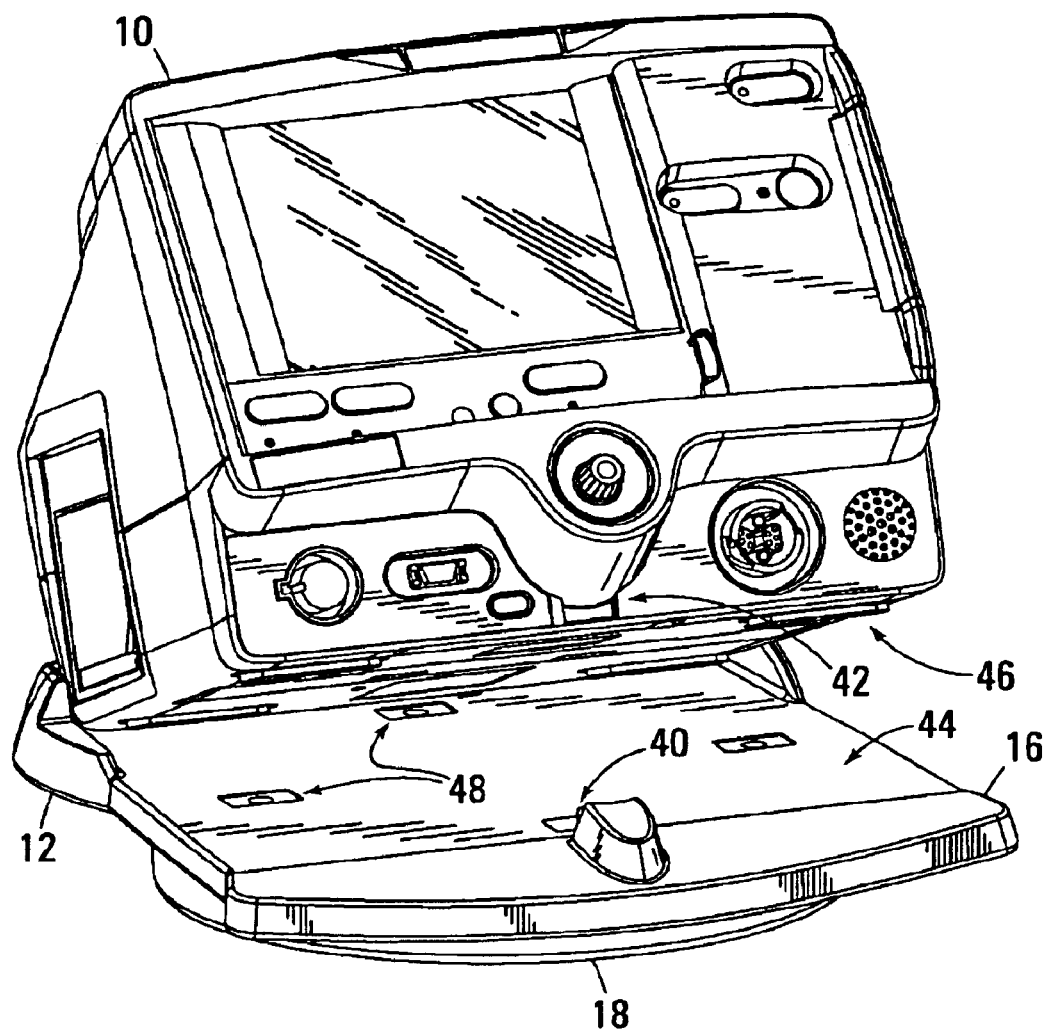
FIG. 2 is a perspective view of the defibrillator of FIG. 1 engaging or disengaging from the docking station.

FIG. 2 shows defibrillator 10 disengaging from docking station 12. By lifting handle 14 (not shown in FIG. 2), an operator has caused a front clamp 40 to disengage from a recess 42 on the front side of defibrillator 10. Defibrillator 10 is still engaged to rear clamps (not shown in FIG. 2), but defibrillator 10 can easily be disengaged from the rear clamps. Once defibrillator 10 is disengaged from docking station 12, defibrillator 10 may be transported wherever desired. This is especially advantageous when defibrillator 10 is needed in an area too small to accommodate the crash cart, or when a patient is being transported on a gurney or mobile bed.

As defibrillator 10 is lifted, the top surface 44 of cover 16 is revealed. Top surface 44 is generally a flat surface that supports the underside 46 of defibrillator 10. The mounting holes 48 are unrelated to support of defibrillator 10. Rather, mounting holes 48 allow docking station 12 to be securely mounted to a crash cart or other structure, as will be shown in FIG. 4.

FIG. 2 also shows one way in which defibrillator 10 may engage with docking station 12. In particular, the operator may engage the rear of defibrillator 10 with rear clamps first, then lower defibrillator 10 onto cover, engaging front clamp 40 with recess 42. This is not the only way for defibrillator 10 to engage with docking station 12, however. The operator may, for example, engage front clamp 40 first and the rear clamps afterward.

Figure 3:
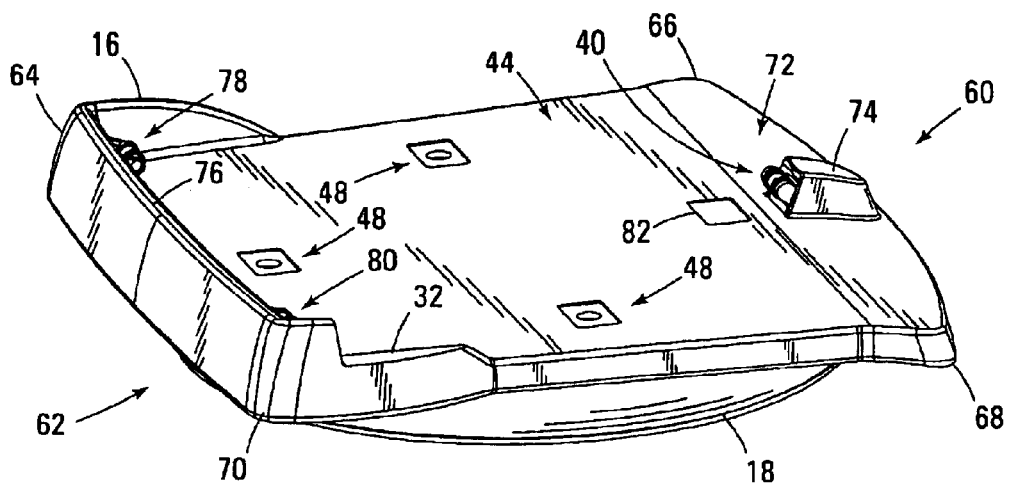
FIG. 3 is a perspective view of the docking station of FIG. 1.

FIG. 3 is a perspective view of docking station 12. The front side of docking station 12 is indicated by reference numeral 60 and the rear side is indicated by reference numeral 62. As shown in FIG. 3, cover 16 may include a substantially flat and substantially square-shaped top surface 44. Corners 64, 66, 68, 70 may bulge outward slightly to give the operator leverage to rotate cover 16. Front ledge 72 curves down slightly, thereby giving the operator extra room for access to front-mounted inputs or outputs on defibrillator 10, as shown in FIG. 1.

Front clamp 40 is housed by front clamp housing 74 in cover 16. As shown in FIG. 3 and as will be described in more detail below, front clamp 40 may comprise a spring-loaded roller clamp. When defibrillator 10 is engaged or disengaged with docking station 12, the spring-loaded roller clamp may be pushed back into front clamp housing 74. When pressure against the spring-loaded roller clamp is released, front clamp 40 projects outward from front clamp housing 74.

Rear side 62 includes a raised brim 76. As shown in FIG. 3, brim 76 may also wrap around corners 64, 70. Brim 76 may perform at least two functions. First, brim 76 may house rear clamps 78, 80. Second, brim 76 may provide a guide for the operator in steering defibrillator 10 into engagement with docking station 12. Brim 76 may be shaped to suit particular defibrillators. For example, brim 76 includes notch 32, which gives the operator access to the built-in printer 34 in defibrillator 10. Brim 76 may be further shaped to accommodate power cables, data cables or other projections from a defibrillator.

Figure 4:
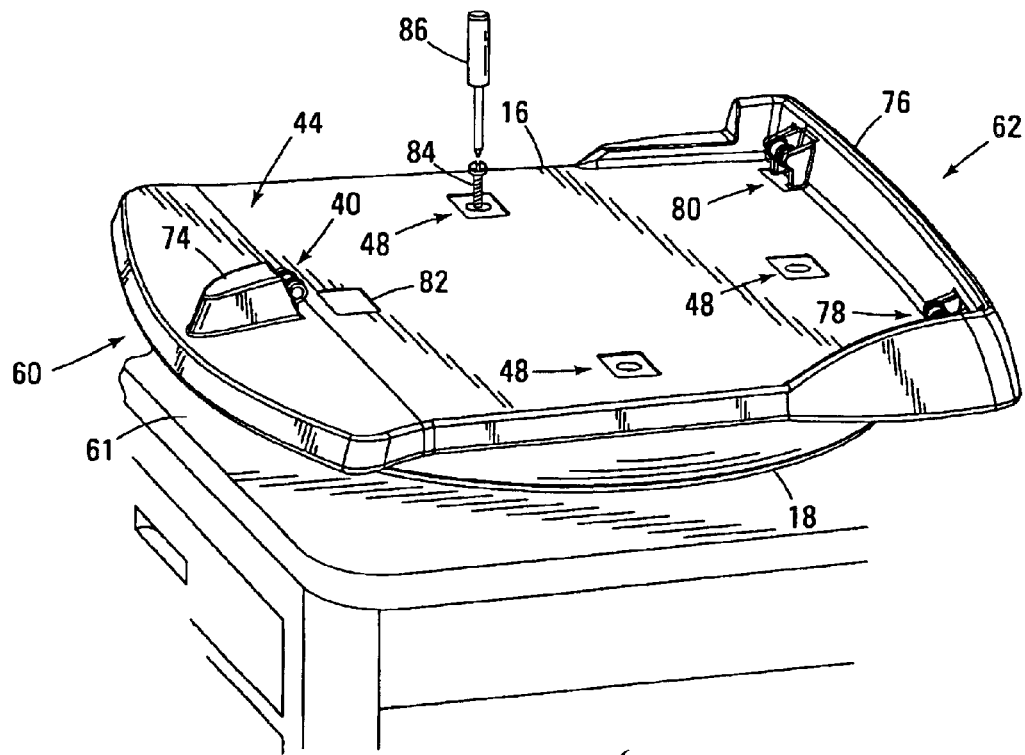
FIG. 4 is a perspective view of the docking station of FIG. 1 from a different angle, further demonstrating a mounting technique.

FIG. 4 is a perspective view of docking station 12 from another angle. FIG. 4 shows rear clamps 78, 80 housed in brim 76. Rear clamps 78, 80 may comprise roller clamps, and need not be spring-loaded. As will be described more fully below, rear clamps 78, 80 may be different from front clamp 40, although the invention also encompasses the variation in which rear clamps 78, 80 and front clamp 40 are identically constructed.

FIG. 4 further illustrates a technique for mounting docking station 12 to a crash cart 61 or other structure. Top surface 44 includes three mounting holes 48. Structure 82 is not a mounting hole, but rather is a feature related to operation of front clamp 40. A fastener such as a screw 84 is inserted into a mounting hole, which is large enough to accommodate the head of screw 84. The head of screw 84 therefore does not seat against top surface 44. Mounting holes (not shown in FIG. 4) on the bottom side of base 18 may be aligned with mounting holes 48, but the mounting holes in the base are not large enough to accommodate the head of screw 84. When screw 84 is driven into a crash cart 61 or other structure with a screwdriver 86, the head of screw 84 seats against the inner surface of base 18, thereby mounting docking station 12 to the crash cart 61 or other structure.

Cover 16 and base 18 may be formed from any of a number of materials, such as metal or plastic. Cover 16 and base 18 may be formed from the same material or may be formed from different materials. In one embodiment, cover 16 and base 18 are made from plastic and are injection molded from a blend of polycarbonate and acrylonitrile-butadiene-styrene resin, such as Bayblend™ plastic, commercially available from Bayer Corporation. Plastic of this type is easily molded, has good impact resistance and good rigidity and dimensional stability.

Figure 5:
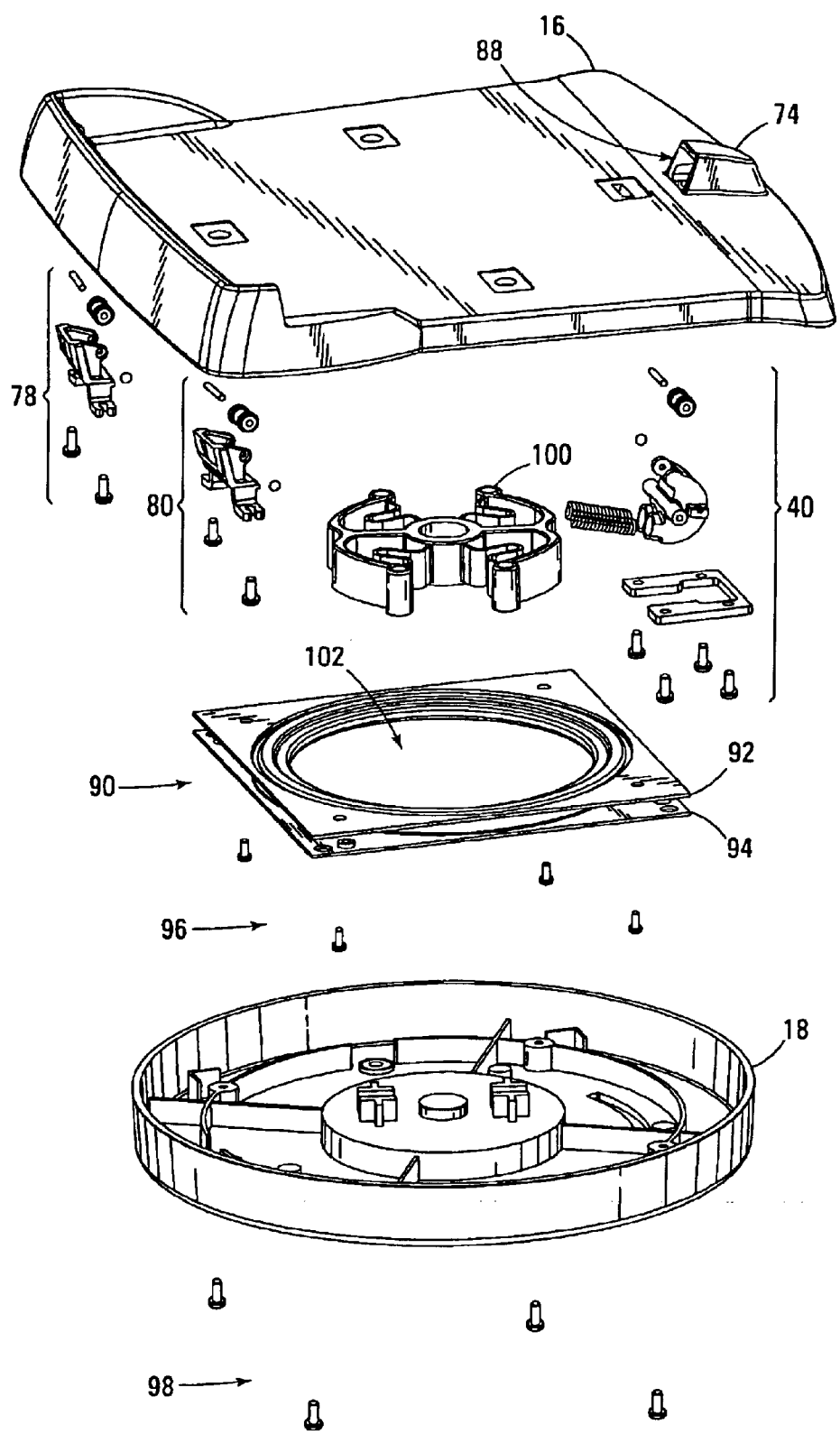
FIG. 5 is an exploded view of the docking station of FIG. 1.

FIG. 5 is an exploded view that demonstrates the interior components and assembly of docking station 12. The view of cover 16 in FIG. 5 is similar to the view of cover 16 in FIG. 3, except that is locking clamps 40, 78, 80 are shown separately. Consequently, the opening 88 in front clamp housing 74, through which a portion of locking clamp 40 protrudes, is visible. Locking clamps 40, 78, 80 will be described in more detail below.

A turntable mechanism 90, sometimes referred to conventionally as a "lazy susan bearing" or a "lazy susan turntable," couples cover 16 to base 18. Turntable mechanism 90 comprises an upper platter 92 and a lower platter 94 coupled to one another. Although platters 92, 94 cannot be pulled apart, platters 92, 94 are free to rotate relative to one another. In a typical implementation, turntable 90 includes a reduced friction mechanism, such as a ball bearing mechanism, to facilitate rotation. Turntable 90 is typically constructed from metal, but can be fabricated of plastic for lighter loads.

Upper platter 92 is coupled to cover 16 with fasteners such as screws 96. Lower platter 94 is coupled to base 18 with fasteners such as screws 98. When cover 16, turntable 90 and base 18 are coupled in this fashion, cover 16 cannot be separated from base 18, but cover 16 and base 18 can be rotated relative to one another. Turntable 90 further aids in weight distribution when a load such as the weight of defibrillator 10 is placed upon cover 16, allowing cover to rotate smoothly and without binding.

In one embodiment of the invention, cover 16 and base 18 can be rotated relative to one another but the rotation is regulated. In particular, cover 16 can rotate relative to base 18 through a number of stable positions. A spring arm device 100, coupled to base 18 as will be described below, interacts with a crown-shaped structure on the underside of cover 16 through a center opening 102 in turntable 90 and regulates rotation. In particular, spring arm device 100 interacts with the crown-shaped structure to provide a stepping action in which turntable 90 rotates among a series of locking angular positions. In the locking angular positions, cover 16 resists rotation relative to base 18, but the resistance can be overcome by the application of sufficient torque. An applied torque of approximately three foot-pounds (approximately four newton-meters), for example, may be sufficient to rotate cover 16 relative to base 18.

Figure 6:
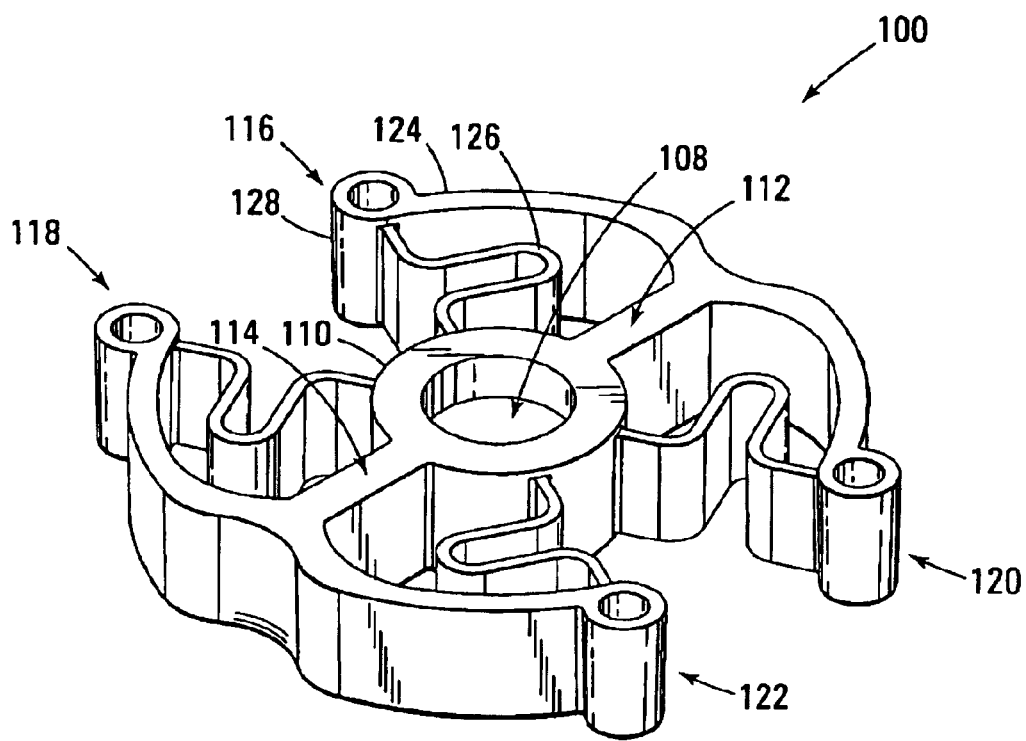
FIG. 6 is a perspective drawing of a spring arm that may be used in the docking station of FIG. 1.

FIG. 6 is a perspective drawing of spring arm 100, which is an exemplary embodiment of a spring mechanism. Spring arm 100 includes a central body 110. Central body 110 may include a central depression 108. Main arms 112, 114 protrude from central body 110 in opposite directions. Central body 110 and main arms 112, 114 support four spring elements 116, 118, 120, 122. Spring elements 116, 118, 120, 122 are arranged symmetrically.

Spring element 116, for example, includes a large spring member 124 and a small spring member 126 coupled to a cylinder 128. In one embodiment, spring arm 100 is made from plastic and are injection molded from Delrin™ acetal resin, commercially available from du Pont de Nemours and Company, of Wilmington, Del. Material of this kind produces a spring arm that can deform without fracturing or shattering. This material also has a low coefficient of friction, which promotes smooth interaction between spring arm 100 and the underside of cover 16.

Figure 7:
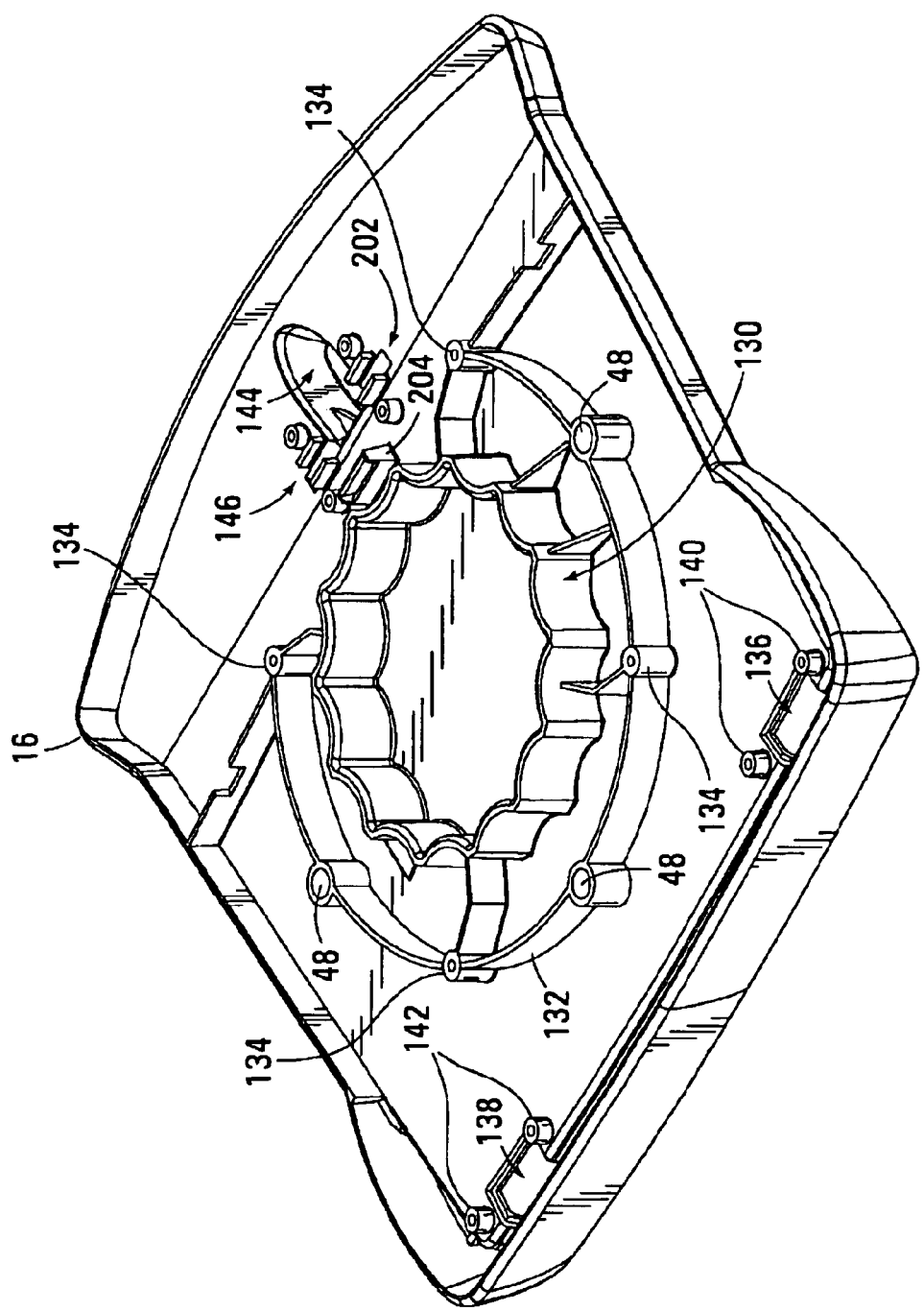
FIG. 7 is a perspective view of the underside of a cover associated with the docking station of FIG. 1.

FIG. 7 is a perspective view of the underside of cover 16. Cover 16 includes a crown 130, which takes the form of a crown-shaped structure that receives spring element 100 as will be described below. Crown 130 may be integrally formed with cover 16.

FIG. 7 also shows supporting rib structure 132, which provides structural integrity to cover 16. Rib structure 132 supports crown 130 and sleeves for mounting holes 48. Rib structure 132 further supports fittings 134 for fasteners 96 (not shown in FIG. 7) that couple turntable 90 (not shown in FIG. 7) to cover 16.

Further, FIG. 7 shows openings 136, 138 and mounting structures 140, 142, which are used to mount rear clamps 78, 80. Cover 16 also has an opening 144, which forms the underside of front clamp housing 74, and front mounting structures 146, which are used to mount front clamp 40.

Figure 8:
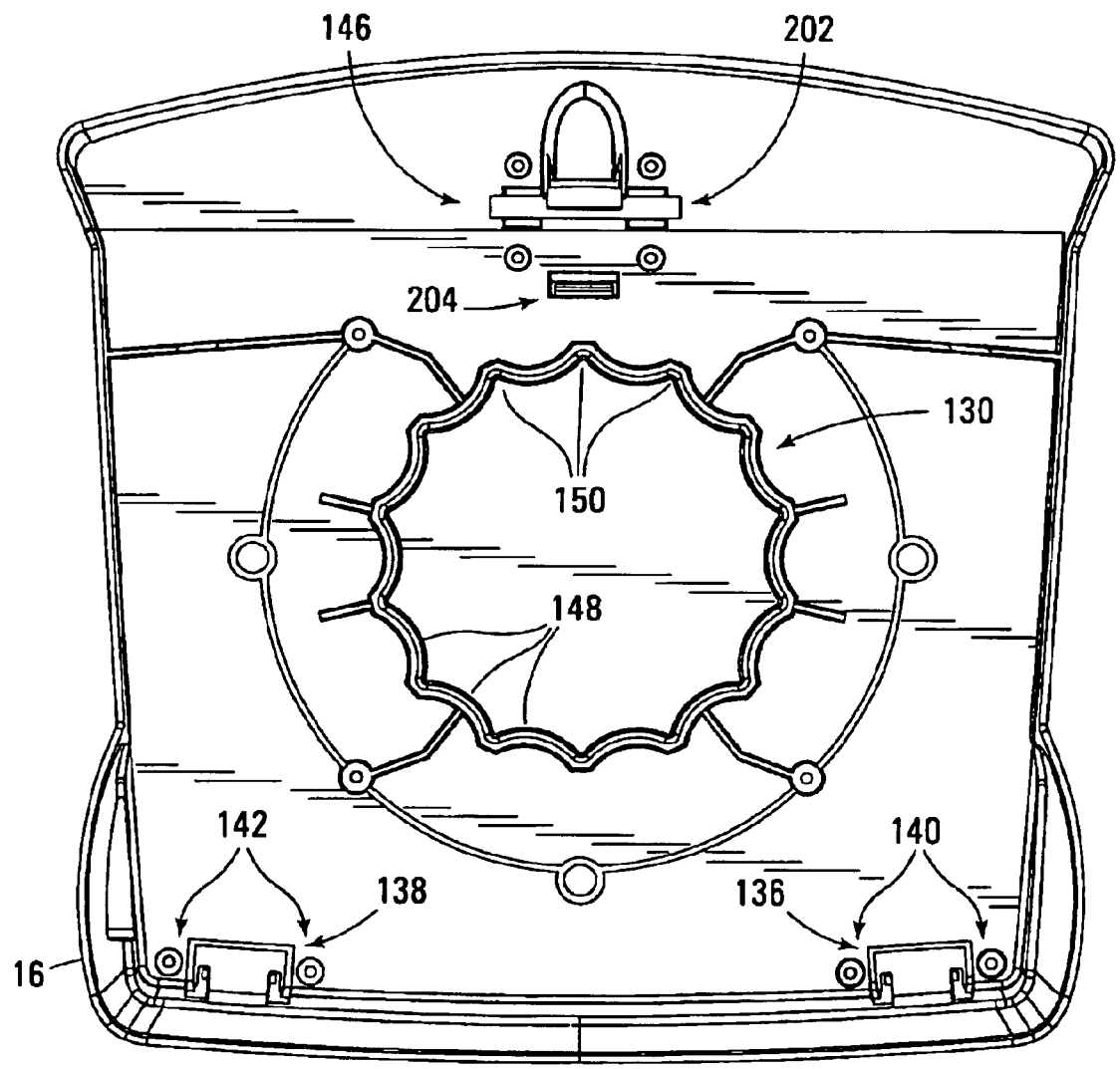
FIG. 8 is a plan view of the underside of a cover associated with the docking station of FIG. 1.

FIG. 8 is a plan view of the underside of cover 16. This view shows the shape of crown 130. Crown 130 is a crown-shaped ring comprising rounded indentations 148 protruding into the ring. Rounded indentations 148 define detents 150, which are the points inside crown 130 that are farthest from the center of crown 130. In FIG. 8, there are sixteen indentations 148 and sixteen detents 150.

Figure 9:
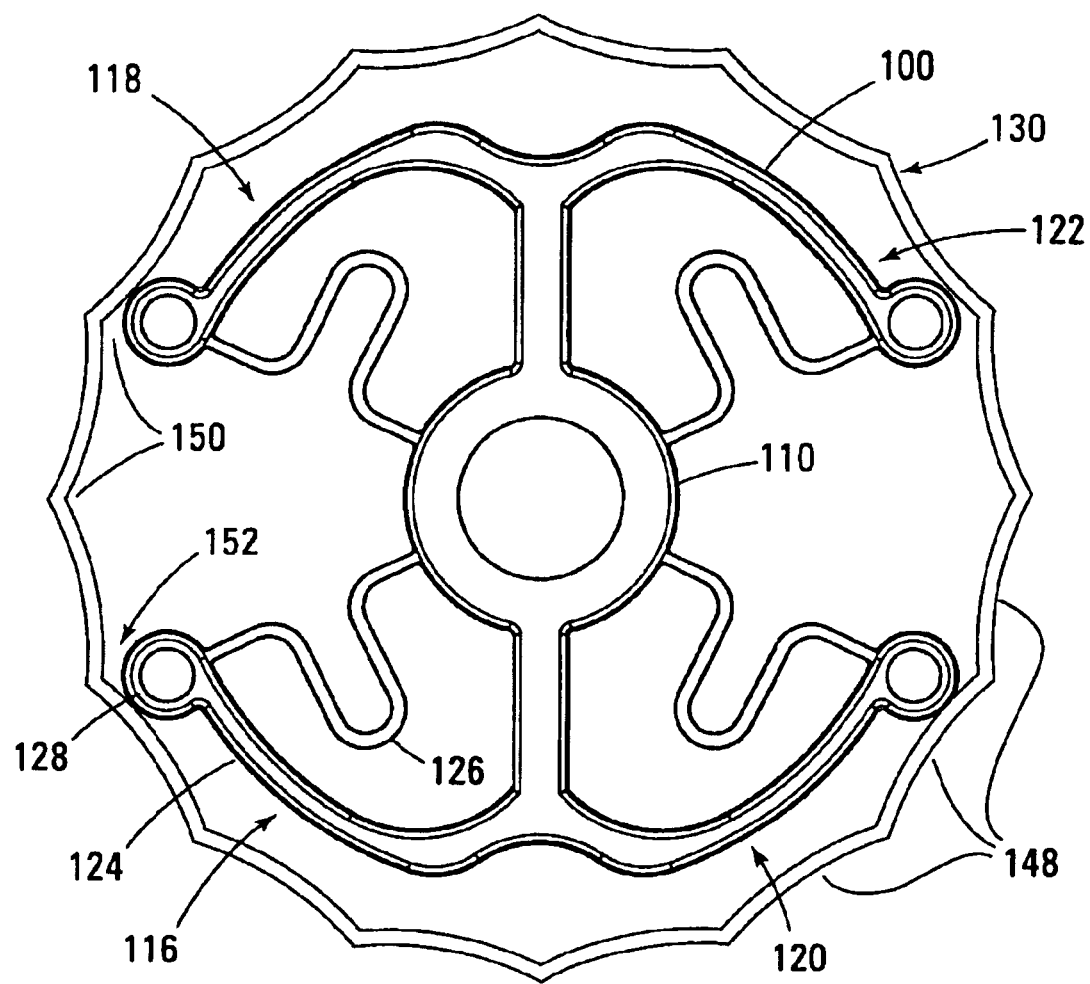
FIG. 9 is a plan view of a crown on the underside of a cover associated with the docking station, engaged with the spring arm of FIG. 6 in a stable configuration.

FIG. 9 shows the engagement between crown 130 and spring arm 100. Spring arm 100 engages crown 130 in a stable configuration, i.e., spring arm 100 is as fully expanded inside crown 130 as crown 130 permits. In a typical implementation, the natural shape of spring arm 100 seats spring arm 100 snugly inside crown 130 with very little compression of any spring elements. In a stable configuration, spring elements 116, 118, 120, 122 exert very little force against crown 130 because their shape is close to the shape spring elements 116, 118, 120, 122 would have when outside crown 130. The engagement of four symmetrical spring elements 116, 118, 120, 122 with crown 130 reduces wobbling during rotation. Notably, cylinder 128 of spring element 116 need not necessarily rest fully in the nearest detent 152.

Figure 10:
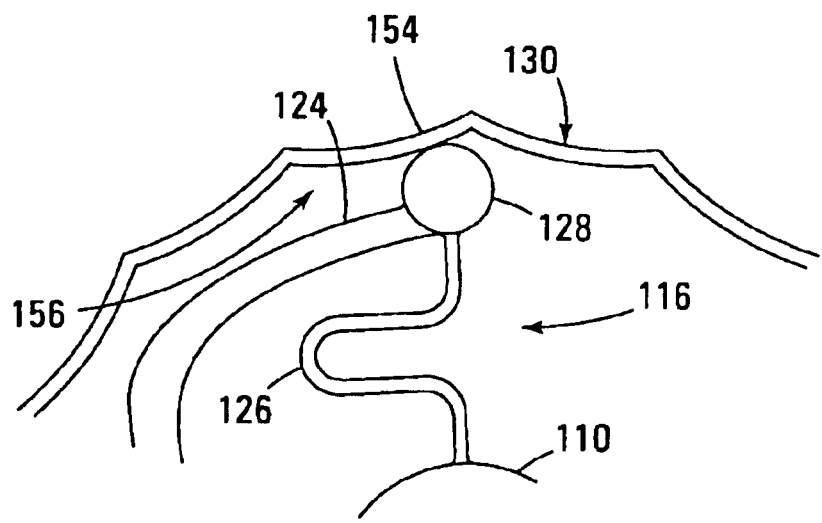
FIG. 10 is a plan view of a spring element of the spring arm of FIG. 6 engaging the crown of FIG. 9, with the spring arm in a stable configuration.
Figure 11:
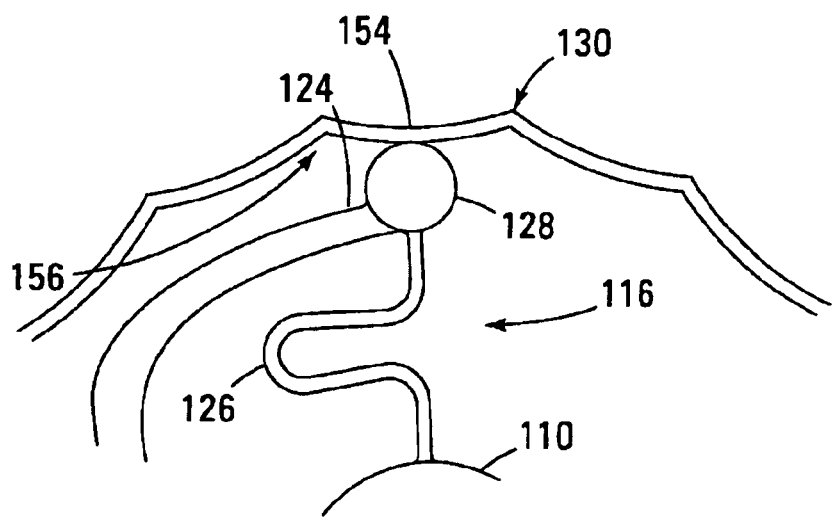
FIG. 11 is a plan view of the spring element of FIG. 6 engaging the crown of FIG. 9, with the spring arm in an unstable configuration.

FIGS. 10 and 11 illustrate compression of exemplary spring element 116 when spring arm 100 is rotated relative to crown 130. FIG. 10 shows spring element 116 engaging crown 130 in a stable configuration, and FIG. 11 shows spring element 116 engaging crown 130 in an unstable configuration due to rotation. During rotation, indentation 154 of crown 130 pushes cylinder 128 closer to central body 110. As a result, large spring member 124 bends inward and small spring member 126 deforms due to compression. The deformations store potential energy and cause cylinder 128 to exert a greater force against crown 130. When cylinder 128 nears detent 156, large spring member 124 and small spring member 126 push cylinder 128 outward, and spring arm returns to a stable configuration.

As noted above, cylinder 128 may be formed from a plastic such as Delrin™, and crown 130 may be formed from a plastic such as Bayblend™. There is a low coefficient of friction between such materials. Cylinder 128 glides smoothly over indentation 154 with little wear or tear to either component.

As will be shown below, spring arm 100 is coupled to base 18 and does not rotate relative to base 18. Spring arm 100 does rotate relative to cover 16, however, as shown in FIGS. 9, 10 and 11, i.e., crown 130 rotates around spring arm 100. In this way, the rotation of cover 16 relative to base 18 is not a smooth rotation. Rather, cover 16 steps through sixteen stable positions. As a result, defibrillator 10, when docked in docking station 12, will not rotate freely. When crash cart is moved or is parked on an unbalanced surface, defibrillator 10 will not swivel uncontrollably. Medical personnel can, however, apply a torque to defibrillator 10 or cover 16 to rotate defibrillator 10 to any desired angle.

Figure 12:
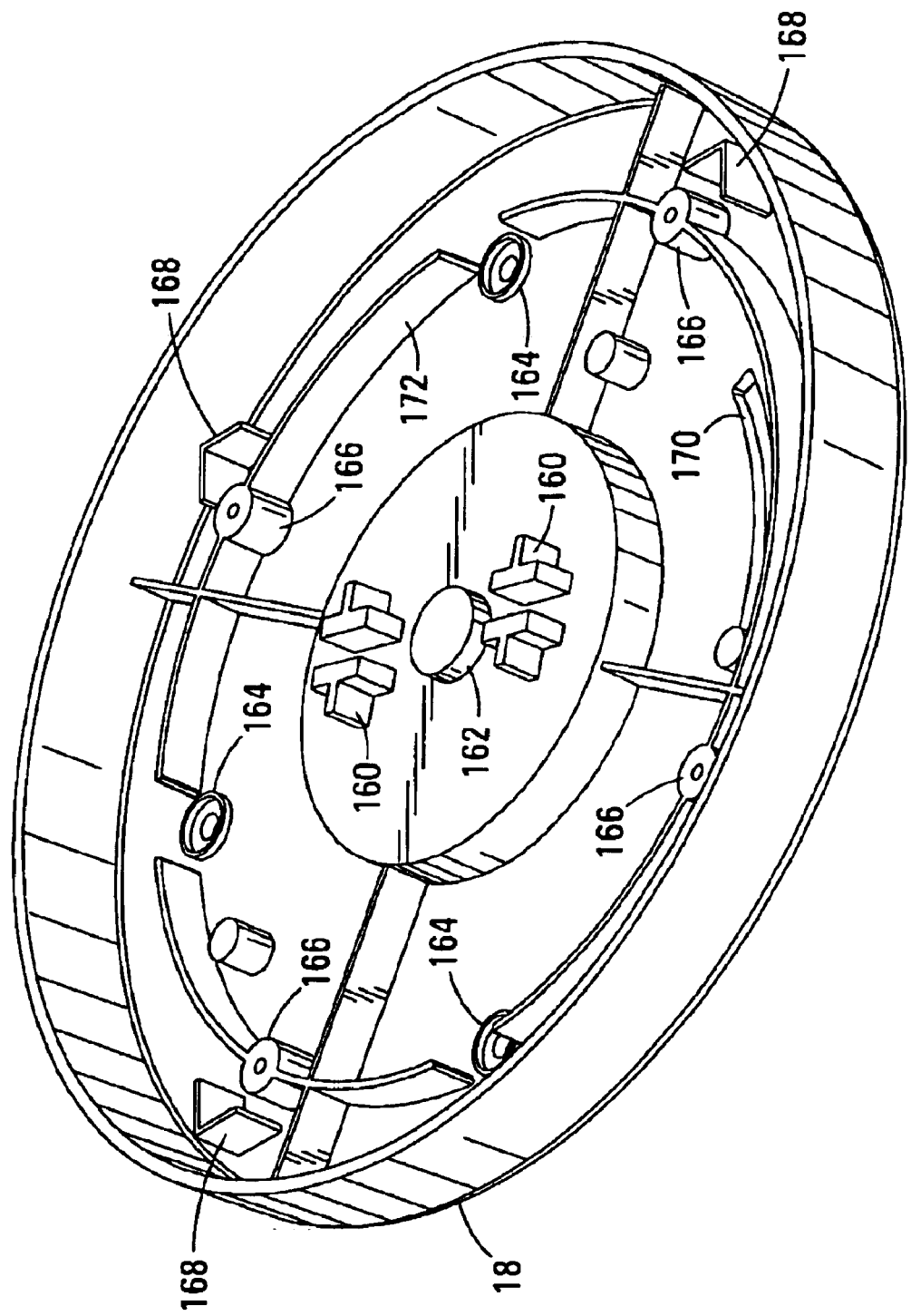
FIG. 12 is a perspective view of a base of the docking station of FIG. 1.

FIG. 12 is a perspective view of the interior of base 18. The center region includes brackets 160 that receive main arms 112, 114 of spring arm 100. The center region may also include a protrusion 162, which is received by depression 108 of central body 110.

FIG. 12 further shows mounting holes 164. Base 18 can be rotated relative to cover 16 so that mounting holes 164 align with mounting holes 48 in cover 16. Mounting holes 48 in cover 16 provide access to mounting holes 164 in base 18. As shown in FIG. 4, a fastener such as a screw 84 may be seated against the inner surface of base 18 to mount docking station 12 to a crash cart or other structure.

FIG. 12 also shows support fittings 166 for fasteners 98 (not shown in FIG. 12) that couple lower platter 94 of turntable 90 (not shown in FIG. 7) to base 18. In addition, base 18 may include ribs 168 that receive lower platter 94. Ribs 168 are useful in aligning lower platter 94 during assembly. An access slot 170 may allow the assembler to rotate lower platter 94 into position for assembly. Base 18 may also include a rib structure 172 for structural integrity and for support of fittings 166.

FIG. 13 is an exploded view of one of an exemplary coupling mechanism, i.e., front clamp 40. Front clamp 40 includes a roller 180 on a spindle 182 that couples to a rocker body 184. Rocker body 184 includes a bracket 186 that receives roller 180 and spindle 182. Roller 180 and spindle 182 may be secured with a locking ring 188. Rocker body 184 is secured to front mounting structures 146 of cover 16 (not shown in FIG. 13) with mounting bracket 190 and fasteners 192. Fasteners 192 may be screws.

Rocker body 184 includes sockets 194 that receive expansive springs 196. In addition, rocker body 184 includes an axle member 198 and a stop block 200. Rocker body 184, including sockets 196, axle member 198 and stop block 200, may be integrally formed form an injection molded plastic such as Delrin™.

FIG. 14 shows front clamp 40 assembled. When mounted to cover 16, roller 180 and bracket 186 of rocker body 184 are protected by front clamp housing 74. Axle member 198 seats in a slot 202 defined by the underside of cover 16. Springs 196 seat in sockets 194 and bear against barrier 204, which likewise is defined by the underside of cover 16. Slot 202 and barrier 204 are shown in FIGS. 7 and 8. When cover 16 is injection molded, barrier 204 may be hollow, which may result in an artifact on top surface 44. Structure 82, shown in FIGS. 3 and 4, is such an artifact. Springs 196 push against barrier 204 and sockets 194, causing rocker body 184 to pivot around axle member 198, thereby causing roller 180 and bracket 186 of rocker body 184 to project through opening 88. Stop block 200 bears against the underside of cover 16, impeding further projection through opening 88.

Front clamp 40 is a spring-loaded roller clamp. When defibrillator 10 is engaged with docking station 12, defibrillator 10 pushes roller 180 and bracket 186 into front clamp housing 74. As a result, rocker body 184 pivots around axle member 198, causing springs 196 to compress between sockets 196 and barrier 204. When defibrillator 10 is docked, springs push roller 180 and bracket 186 outward into recess 42 of defibrillator 10. Similarly, when defibrillator 10 is disengaged from docking station 12, defibrillator 10 pushes roller 180 and bracket 186 into front clamp housing 74, and roller 180 and bracket 186 spring back when defibrillator 10 is free.

FIG. 15 is an exploded view of an exemplary rear clamp 80. Rear clamp 80 includes a roller 210 on a spindle 212 that couples to a main body 214. Main body 184 includes a bracket 216 that receives roller 210 and spindle 212. Roller 210 and spindle 212 may be secured with a locking ring 218. Main body 214 may further include mounting brackets 220. Fasteners 222 such as screws couple mounting brackets 220 to mounting structures 142 on cover 16. Roller 210 and a portion of main body 184 protrude through opening 138 in cover 16.

Unlike front clamp 40, rear clamp 80 is not spring loaded. When defibrillator 10 engages docking station 12 as shown in FIG. 2, defibrillator 10 may engage rear clamps 78, 80 first, and need not push rear clamps 78, 80 to make the engagement.

The invention can provide one or more advantages. In particular, docking station 12 holds defibrillator 10 securely. Defibrillator 10 may be transported rapidly on a crash cart without becoming dislodged from docking station 12. Other techniques for securing a defibrillator to a crash cart, such as strapping the defibrillator to the crash cart, prevent rapid removal of the defibrillator from the crash cart. When docked with docking station 12, by contrast, defibrillator 10 may be quickly undocked from docking station 12 for transportation to any convenient site.

Defibrillator 10 can be rotated while docked in docking station 12. In an embodiment described above defibrillator 10 can be rotated 360 degrees. When docking station 12 is mounted to a crash cart, it is less important to orient the crash cart so that defibrillator 10 is facing in the right direction. Rather, defibrillator 10 can simply be turned to a desired position by rotating cover 16 relative to base 18.

In one of the embodiments described above, cover 16 rotates in discrete steps. Stepped rotational freedom is advantageous in many respects. First, defibrillator 10 will not swivel uncontrollably when docked. When defibrillator 10 is being rushed via a crash cart to a patient, uncontrolled swiveling is undesirable. Also, as shown in FIG. 1, controls 22 of defibrillator 10 may be located off-center, and operation of the controls may introduce torque to defibrillator 10 and docking station 12. Torque may also be introduced by, for example, coupling defibrillation electrodes to defibrillator electrode receptacle 28 and pulling the electrodes toward a patient. Without some restriction of rotational freedom, defibrillator 10 may rotate to an inconvenient orientation and may be more difficult to operate. An operator may try to push a button, for example, only to have defibrillator 10 swivel in response. With stepped rotational freedom, docking station 12 resists the applied torque, and the operator need not worry about controls 22 moving. Access to inputs or outputs is also easier when defibrillator 10 is held steady. The particular embodiment employing a spring arm and a crown is further advantageous in that it uses few moving parts and requires no separate locking mechanism.

Although various coupling mechanisms may be employed, roller clamps are advantageous in several respects. Roller clamps need no separate locking latch. Roller clamps are also durable and can perform well after numerous dockings and undockings. Roller clamps also make docking and undocking simple: a medical device may be easily docked simply by pushing the medical device onto the docking station, and may be easily undocked by lifting the medical device off the docking station.

Various embodiments of the invention have been described. These embodiments are illustrative of the practice of the invention. Various modifications may be made without departing from the scope of the claims. For example, the docking station is not limited to use with a defibrillator. Other medical devices likewise may be secured to structures such as crash carts with the invention. Furthermore, cover 16 is merely an exemplary platform for a defibrillator. Platforms may be shaped in a variety of ways, and in particular, may be shaped to accommodate and support a particular model of medical device. Similarly, the base need not be shaped like base 18. The invention encompasses docking stations with bases of all shapes.

The invention encompasses docking stations that include a platform that rotate in relation to a base. The invention encompasses all degrees of rotation, and is not limited to the stepped rotation described above. For example, a platform may rotate freely with respect to a base, and may also be locked in place with a mechanism such as a locking lever and/or a clutch mechanism.

The spring mechanism need not be a spring arm as shown in the figures. A spring mechanism may, for example, include fewer than four spring elements. It may be possible to form the spring element integrally with the platform or the base. Similarly, the crown need not be shaped as shown in the figures, and the spring mechanism need not engage the crown as shown. The spring mechanism may, for example, engage the exterior of the crown, rather than the interior as shown in FIG. 9.

The crown may be coupled to the base, rather than the platform. Similarly, the spring mechanism may be coupled to the platform rather than the base.

The coupling mechanisms need not be roller clamps. The coupling mechanisms may be, for example, latches or manually operated locks. In an embodiment above, roller clamps on the docking station engaged recesses on a medical device, but the invention also encompasses, for example, roller clamps on a defibrillator that engage recesses on the docking station.

These and other embodiments are within the scope of the following claims.

What is claimed is:

1. A device comprising:
   a platform that supports a defibrillator;
   a coupling mechanism coupled to the platform that engages and holds the defibrillator on the platform; and
   a base coupled to the platform, the platform having some freedom to rotate relative to the base.

2. The device of claim 1, wherein the coupling mechanism is a roller clamp.

3. The device of claim 1, wherein the coupling mechanism is a spring-loaded roller clamp.

4. The device of claim 1, wherein the coupling mechanism is a first coupling mechanism that engages and holds a first side of the defibrillator, the device further comprising a second coupling mechanism that engages and holds a second side of the defibrillator.

5. The device of claim 1, further comprising:
   a crown coupled to one of the platform and the base; and
   a spring mechanism coupled to the other of the platform and the base,
   wherein the spring mechanism engages the crown, and wherein rotation of the platform relative to the base causes at least a portion of the spring mechanism to deform and resist the rotation.

6. The device of claim 1, further comprising a turntable comprising an upper plate and a lower plate, the upper plate coupled to the platform and the lower plate coupled to the base.

7. The device of claim 1, wherein the base includes a mounting hole for mounting the base to a structure with a fastener.

8. The device of claim 7, wherein the platform includes a mounting access hole that can be aligned with the mounting hole.

9. The device of claim 1, further comprising a crash cart fixedly coupled to the base.

10. A method comprising:
    engaging a medical device with a coupling mechanism on a docking station;
    holding the medical device with the coupling mechanism; and
    rotating at least one portion of the docking station relative to another portion of the docking station.

11. The method of claim 10, herein the medical device is a defibrillator.

12. The method of claim 10, further comprising:
    releasing the medical device from the coupling mechanism; and
    disengaging the medical device from the coupling mechanism on the docking station.

13. The method of claim 10, further comprising retracting at least a portion of the coupling mechanism when engaging the medical device.

14. The method of claim 13, herein holding the medical device with the coupling mechanism comprises extending the poition of the coupling mechanism.

15. A device comprising:
   a platform that supports a defibrillator;
   a first coupling mechanism coupled to the platform that engages and holds a first side of the defibrillator; and
   a second coupling mechanism that engages and holds a second side of the defibrillator.

16. The device of claim 15, herein the first and second coupling mechanisms are roller clamps.

17. The device of claim 15, wherein at least one of the first and second the coupling mechanisms is a spring-loaded roller clamp.

18. The device of claim 15, wherein the first coupling mechanism engages and holds the front of the defibrillator and wherein the second coupling mechanism engages and holds the rear of the defibrillator.

19. The device of claim 15, further comprising a base coupled to the platform, the platform having some freedom to rotate relative to the base.

20. The device of claim 19, further comprising a turntable comprising an upper plate and a lower plate, the upper plate coupled to the platform and the lower plate coupled to the base.

21. A device comprising:
   a platform that supports a medical device;
   a base coupled to the platform;
   a crown coupled to one of the platform and the base; and
   a spring mechanism coupled to the other of the platform and the base,
   wherein the spring mechanism engages the crown, and wherein rotation of the platform relative to the base is restricted by the engagement of the spring mechanism and the crown.

22. The device of claim 21, wherein rotation of the platform relative to the base causes at least a portion of the spring mechanism to deform.

23. The device of claim 21, wherein the platform has freedom to rotate 360 degrees relative to the base.

24. The device of claim wherein 21, the platform has freedom to rotate in steps relative to the base.

25. The device of claim 21, further comprising a turntable comprising an upper plate and a lower plate, the upper plate coupled to the platform and the lower plate coupled to the base.

26. The device of claim 25, wherein the turntable has a center opening, and wherein the spring mechanism engages the crown in the center opening.

27. A defibrillator comprising:
   a first docking structure that engages a first coupling mechanism of a docking station; and
   a second docking structure that engages a second coupling mechanism of the docking station.

28. The defibrillator of claim 27, wherein the first docking structure comprises a recess that receives the first coupling mechanism.

29. The defibrillator of claim 28, wherein the first coupling mechanism is a roller clamp and the recess is shaped to receive the roller clamp.

30. A device comprising:
   a platform that supports a medical device;
   a first coupling mechanism coupled to the platform that engages and holds a first side of the medical device on the platform;
   a second coupling mechanism that engages and holds a second side of the medical device;
   a base coupled to the platform, the platform having some freedom to rotate relative to the base; and
   a turntable comprising an upper plate and a lower plate, the upper plate coupled to the platform and the lower plate coupled to the base.

31. The device of claim 30, further comprising a crash cart fixedly coupled to the base.

32. A device comprising:
   a platform that supports a medical device;
   a coupling mechanism coupled to the platform that engages and holds the medical device on the platform;
   a base coupled to the platform, the platform having some freedom to rotate relative to the base, wherein the base includes a mounting hole for mounting the base to the crash cart with a fastener; and
   a crash cart fixedly coupled to the base.

* * * * *

UNITED STATES PATENT AND TRADEMARK OFFICE
CERTIFICATE OF CORRECTION

PATENT NO. : 6,865,418 B2
DATED : March 8, 2005
INVENTOR(S) : Rodney Merry

It is certified that error appears in the above-identified patent and that said Letters Patent is hereby corrected as shown below:

Column 10,
Line 61, "herein" should read -- wherein --.

Column 11,
Lines 4 and 13, "herein" should read -- wherein --.

Signed and Sealed this

Second Day of May, 2006

JON W. DUDAS
*Director of the United States Patent and Trademark Office*